(12) United States Patent  
Wang

(10) Patent No.: US 10,213,279 B2  
(45) Date of Patent: Feb. 26, 2019

(54) DENTURE FIXING ATTACHMENT

(71) Applicant: Je Won Wang, Daejeon (KR)

(72) Inventor: Je Won Wang, Daejeon (KR)

( * ) Notice: Subject to any disclaimer, the term of this patent is extended or adjusted under 35 U.S.C. 154(b) by 0 days.

(21) Appl. No.: 15/120,938

(22) PCT Filed: Feb. 2, 2015

(86) PCT No.: PCT/KR2015/001053  
§ 371 (c)(1),  
(2) Date: Aug. 23, 2016

(87) PCT Pub. No.: WO2015/133733  
PCT Pub. Date: Sep. 11, 2015

(65) Prior Publication Data  
US 2016/0361144 A1    Dec. 15, 2016

(30) Foreign Application Priority Data  
Mar. 6, 2014   (KR) .......................... 10-2014-0026568

(51) Int. Cl.  
*A61C 8/00* (2006.01)

(52) U.S. Cl.  
CPC .......... *A61C 8/0053* (2013.01); *A61C 8/0048* (2013.01); *A61C 8/0062* (2013.01); *A61C 8/0095* (2013.01)

(58) Field of Classification Search  
CPC ... A61C 8/0053; A61C 8/0048; A61C 8/0062; A61C 8/0095; A61C 8/0089;  
(Continued)

(56) References Cited

U.S. PATENT DOCUMENTS 866,304 A * 9/1907 Roach ................ A61C 13/2653  
433/177  
5,194,000 A * 3/1993 Dury .................... A61C 8/0018  
433/173  
(Continued)

FOREIGN PATENT DOCUMENTS

JP    2557047 B2    11/1996  
JP    11-244308 A    9/1999  
(Continued)

*Primary Examiner* — Edward Moran  
*Assistant Examiner* — Drew Folgmann  
(74) *Attorney, Agent, or Firm* — Novick, Kim & Lee, PLLC; Jae Youn Kim

(57) ABSTRACT

Provided is a denture fixing attachment including: a rod-shaped joint member, having an upper end for supporting a denture fixed thereto and a locking protruding portion protruding laterally from a lower portion of the joint member; and an abutment having a coupling portion formed in an outer surface of a lower portion thereof so as to be coupled to a fixture recess formed in the fixture, and a receiving portion formed in an upper portion thereof so as to receive the lower portion of the joint member therein, wherein the receiving portion of the abutment includes a receiving recess for receiving the lower portion of the joint member inserted thereinto, and a stop protruding portion provided in the receiving portion above the receiving recess and having a guide groove disposed adjacent to the stop protruding portion for guiding coupling movement of the locking protruding portion fitted thereinto.

1 Claim, 6 Drawing Sheets

(58) Field of Classification Search
CPC ... A61C 8/0054; A61C 8/0069; A61C 8/0059; A61C 8/0066; A61C 8/0074; A61C 8/005; A61C 13/225; A61C 13/2255; A61C 13/2656; A61C 13/275; A61C 8/0057; A61C 8/0086
See application file for complete search history.

(56) References Cited

U.S. PATENT DOCUMENTS

| | | | | |
|---|---|---|---|---|
| 5,417,570 A | * | 5/1995 | Zuest | A61C 8/0048 433/172 |
| 5,480,304 A | * | 1/1996 | Nardi | A61C 8/0048 433/172 |
| 5,873,722 A | * | 2/1999 | Lazzara | A61C 8/008 433/172 |
| 5,890,902 A | * | 4/1999 | Sapian | A61C 8/0048 433/173 |
| 6,102,702 A | | 8/2000 | Folsom, Jr. et al. | |
| 7,959,439 B2 | * | 6/2011 | Bulloch | A61C 13/2656 433/172 |
| 2008/0227058 A1 | * | 9/2008 | Karmon | A61C 8/005 433/174 |
| 2010/0105005 A1 | * | 4/2010 | Bulloch | A61C 8/0048 433/173 |
| 2016/0015485 A1 | * | 1/2016 | Gonella | A61C 8/0054 433/173 |

FOREIGN PATENT DOCUMENTS

| | | |
|---|---|---|
| JP | 2005-528164 A | 9/2005 |
| KR | 10-2007-0112075 A | 11/2007 |
| KR | 10-0925766 B1 | 11/2009 |
| KR | 10-1042372 B1 | 6/2011 |
| KR | 20-2013-0005969 U | 10/2013 |
| KR | 20-0471489 Y1 | 2/2014 |

* cited by examiner

DENTURE FIXING ATTACHMENT

The present application is a U.S. national stage application of PCT/KR2015/001053 filed on Feb. 2, 2015 designating the United States, and claims foreign priority to Korean Application KR10-2014-0026568 filed on Mar. 6, 2014.

TECHNICAL FIELD

The present invention relates to a denture-fixing attachment used to fix a denture after a dental implant treatment and, more particularly, to a denture-fixing attachment, which has an economic effect due to a simple structure and consequent improvement in productivity, highly efficient workability due to a simplified assembly process, and increased stability in use due to the secure maintenance of engagement force for a long time period and consequent prevention of unexpected release of engagement.

BACKGROUND OF THE INVENTION

Conventionally, when a tooth is pulled out, a false tooth is positioned in place of the pulled-out tooth, or a dental bridge treatment, in which surrounding teeth are employed as pillars and a crown is positioned in place of the pulled-out tooth, is performed, thereby maintaining a patient's oral health.

However, this treatment causes problems in which false teeth or artificial teeth resulting from the bridge treatment are weak in chewing foods, exert a bad influence on surrounding teeth, and may even damage other teeth.

Accordingly, implant treatment has been recently introduced and is being widely administered, and is characterized in that an artificial tooth root is formed, and an artificial tooth, produced so as to appear highly similar to a real tooth, is coupled to the artificial tooth root, so that a patient obtains an effect of using the real tooth.

Such an implant treatment is one dental medical treatment for securely fastening an attachment, to which a false tooth (an artificial tooth) is coupled, to an alveolar bone, and is typically carried out according to the following procedures: an implant recess having female threads formed in an inner peripheral surface thereof, to which a fixture having male threads formed in an outer peripheral surface thereof is screwed, is formed for implantation of the fixture in an alveolar bone having no tooth, the fixture is screwed to the implant recess, an abutment having a joint coupled thereto, to which a false tooth (an artificial tooth) is secured, is engaged with female threads formed in the fixture, a neighboring gum is sutured, and a false tooth (an artificial tooth) is coupled to the top portion of the joint.

In the above implant treatment process, the fixture implanted in the alveolar bone serves as a tooth root, and the attachment including the abutment and the joint is a connection component for integrating the fixture with the false tooth (the artificial tooth).

That is, as described above, the fixture and the attachment constitute an implant structure for securely fixing the false tooth (the artificial tooth) at the correct position, and are preferably formed of a metal material such as, particularly, titanium, having superior physical/chemical strength.

Although a typical prosthetic appliance or a typical false tooth damages surrounding teeth or bones over time, a false tooth (an artificial tooth) fixed by an implant treatment performs the function of the original tooth and has the same shape as the original tooth, and does not decay, so the implanted false tooth can be semi-permanently used.

Korean Patent Registration No. 10-0925766 discloses an attachment for use in implant treatment, which is applied to a dental implant and is milled or prepped into a shape suitable for accepting a dental prosthetic, and in which a recess extends axially upwardly from an axial bottom end of a metallic appendage and is shaped to fit over an O-ball or an O-ring receiver abutment of a dental implant, an abutment including a coupling protrusion is provided, the coupling protrusion is repositioned in a coupling recess formed in an upper portion of a fixture, the abutment is fastened to the fixture using a screw, a prosthesis including a screw hole is provided, and dental cement is put between the abutment and the prosthesis to bond the prosthesis to the abutment.

In addition, Korean Patent Registration No. 10-1042372 discloses an integral-type implant, which includes a screw portion provided at a lower portion of the implant and having threads formed in the outer surface of the screw portion so as to be rotated about one axis and implanted into a dentary bone, and an abutment provided at an upper portion of the implant, the abutment being integrally formed with the screw portion and being capable of being embedded in a gum covering the dentary bone and of being covered with a cap. The abutment includes a gingival level portion, which is brought into contact with the gum, and a protrusion portion, which is provided at an upper portion of the gingival level portion and to which the cap is removably attached. The protrusion portion has a coupling recess extending downward from the top surface thereof in an axial direction, and the coupling recess has a sectional shape that may engage with a driver used to rotate the implant.

In addition, Korean Patent Publication No. 10-2007-0112075 discloses a separable-type abutment for a dental implant, which is fixed to a fixture implanted into an alveolar bone to support a dental prosthesis. The abutment includes a lower member fixed to the fixture, an upper member fixed to the dental prosthesis, and a coupling structure for removably coupling the upper member to the lower member.

However, the above-described conventional attachments have a problem in that a denture cannot be coupled to a denture-fixing attachment when several fixtures implanted into a patient are not arranged parallel to each other, thereby requiring another operation for implanting the fixtures parallel to each other or connection work using additional parts.

To solve this problem, Korean Utility Model Publication No. 20-2013-0005969 (entitled: DENTURE-FIXING ATTACHMENT FREELY ADJUSTABLE IN ANGLE AND POSITION) has been recently devised.

The attachment, as disclosed in the above document, is configured such that, when a denture is connected to a fixture implanted in a slanted direction, the denture can be connected to the fixture without additional parts, thereby enabling a doctor to comfortably and easily perform an implant treatment for a patient.

BRIEF SUMMARY OF THE INVENTION

However, although the conventional denture-fixing attachment, as described above, is capable of fixing a denture to a fixture implanted in a slanted direction, it has a problem of being uneconomical in that productivity and workability are deteriorated due to the complicated structure and the inconvenient assembly process, and a problem of being unstable due to possibility of release of the assembly when used for a long time period.

The present invention is devised to solve the above problems, and an object of the present invention is to provide a denture-fixing attachment, which has an economic benefit due to its simple structure and consequent improvement in productivity, highly efficient workability due to a simplified assembly process, and increased stability in use due to the secure maintenance of engagement force for a long time period and consequent prevention of unexpected release of engagement.

The object of the present invention can be achieved by providing a denture-fixing attachment for freely connecting a denture to a fixture implanted into an alveolar bone in a slanted direction by adjusting the fixing angle of the denture with respect to the fixture, the denture-fixing attachment including a rod-shaped joint member having an upper end for supporting the denture fixed thereto, and an abutment having a coupling portion formed in the outer surface of the lower portion thereof so as to be coupled to a fixture recess formed in the fixture, and a receiving portion formed in the upper portion thereof so as to receive the lower portion of the joint member therein, the receiving portion of the abutment including a receiving recess for receiving the lower end of the joint member inserted thereinto, and a stop protruding portion provided in the receiving portion above the receiving recess and having a guide groove for guiding the coupling movement of a locking protruding portion, protruding outward from the lower end of the joint member, fitted thereinto.

The guide groove may be formed to have a spiral shape.

The upper end and the lower end of the joint member may have hemispherical-shaped surfaces, and the joint member may further include a connection portion between the upper end and the lower end, the connection portion being formed to have a rod shape having a smaller diameter than the diameter of the upper end.

The locking protruding portion may be formed to have an annular shape around the outer peripheral surface of the lower end of the joint member so as to be screwed to the spiral-shaped guide groove.

The guide groove may be formed to have a "⌐" shape.

The denture-fixing attachment according to the present invention constituted as above has an economic effect due to a simple structure and consequent improvement of productivity because the joint member, to which a denture is fixed, and the abutment, to which the joint member is pivotably coupled, have a structure capable of being assembled in a fitting manner, highly efficient workability due to a simplified assembly process, which can be achieved merely by fitting work, and increased stability in use due to structural stability in that the receiving portion for receiving the joint member is formed to have an integral structure and due to the consequent prevention of unexpected release of engagement of a denture for a long time period.

Figure 1:
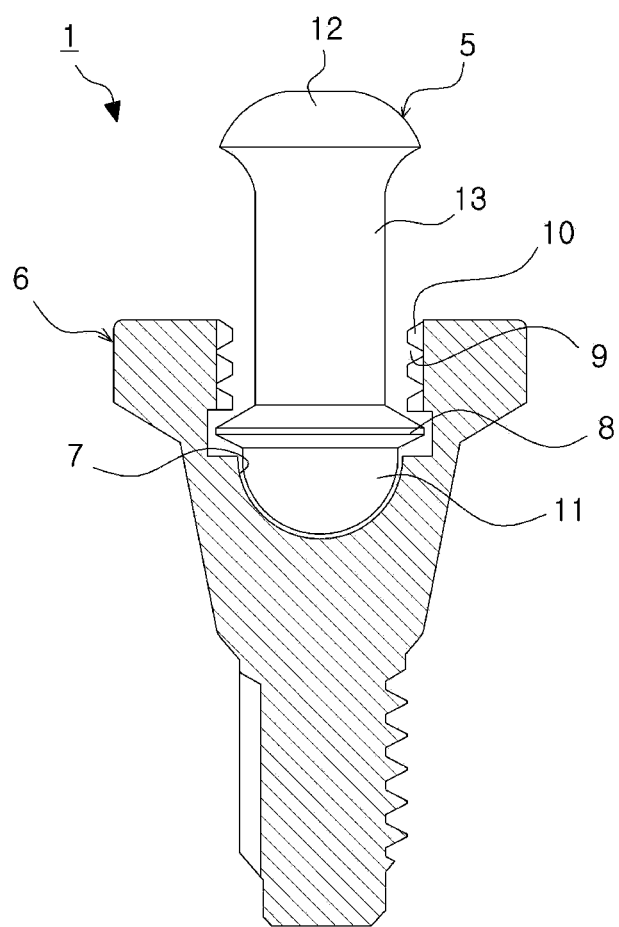
FIG. 1 is a schematic exemplary sectional view showing a denture-fixing attachment according to one embodiment of the present invention.

| | |
|---|---|
| 1: Attachment | 2: Alveolar Bone |
| 3: Fixture | 4: Denture |
| 5: Joint Member | 6: Abutment |
| 7: Receiving Recess | 8: Locking Protruding Portion |
| 9: Guide Groove | 10: Stop Protruding Portion |
| 11: Lower End of Joint Member | 12: Upper End of Joint Member |
| 13: Connection Portion of Joint Member | |

DETAILED DESCRIPTION OF THE INVENTION

Hereinafter, a denture-fixing attachment according to a preferred embodiment of the present invention will be described in detail with reference to the attached drawings.

The present invention may, however, be embodied in different forms and should not be construed as limited to the embodiments set forth herein. Rather, these embodiments are provided so that this disclosure will be thorough and complete, and will fully convey the scope of the present invention to those skilled in the art. In the drawings, the shapes of components are exaggerated for clarity of illustration. In the drawings, the same or similar elements are denoted by the same reference numerals even though they are depicted in different drawings. In the following description, a detailed description of known functions and configurations incorporated herein will be omitted when it may make the subject matter of the present invention rather unclear.

Figure 2:
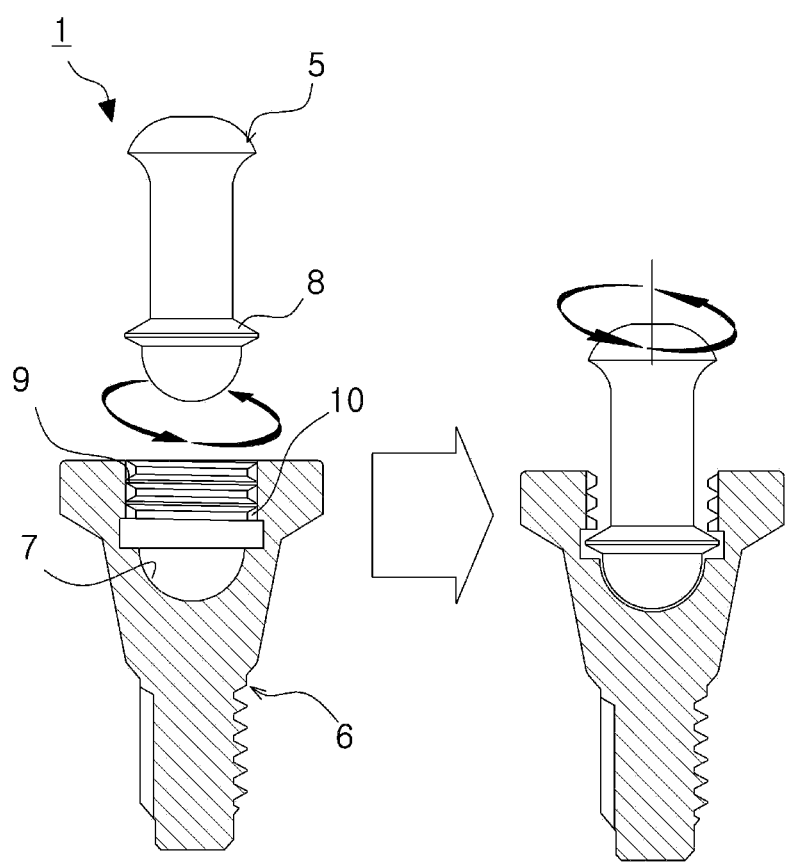
FIG. 2 is a schematic exemplary sectional view showing the assembly state of the denture-fixing attachment according to the embodiment.
Figure 3:
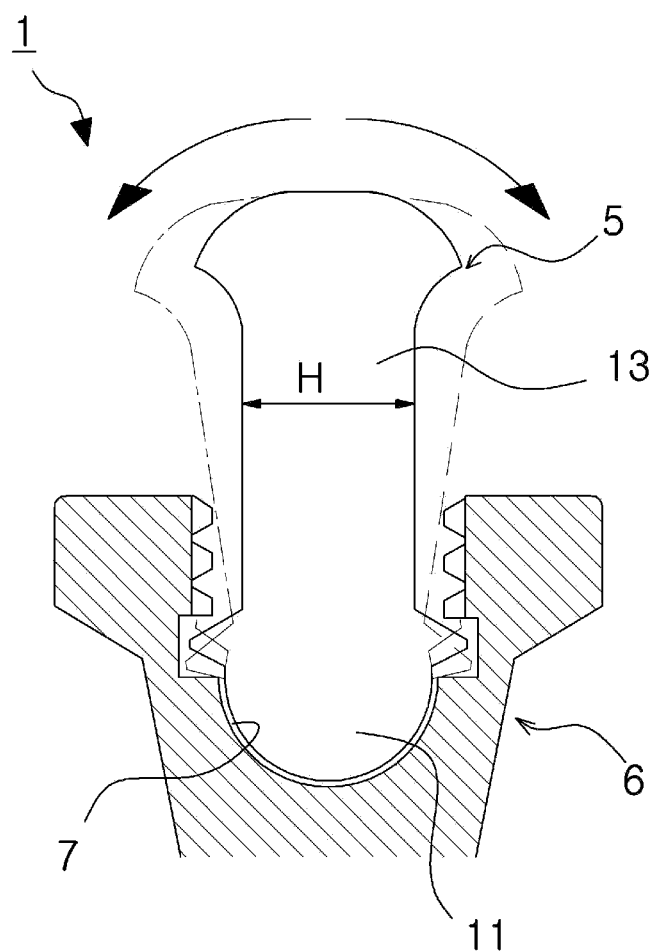
FIG. 3 is an exemplary partially enlarged sectional view showing the operational state of the denture-fixing attachment according to the embodiment.
Figure 4:
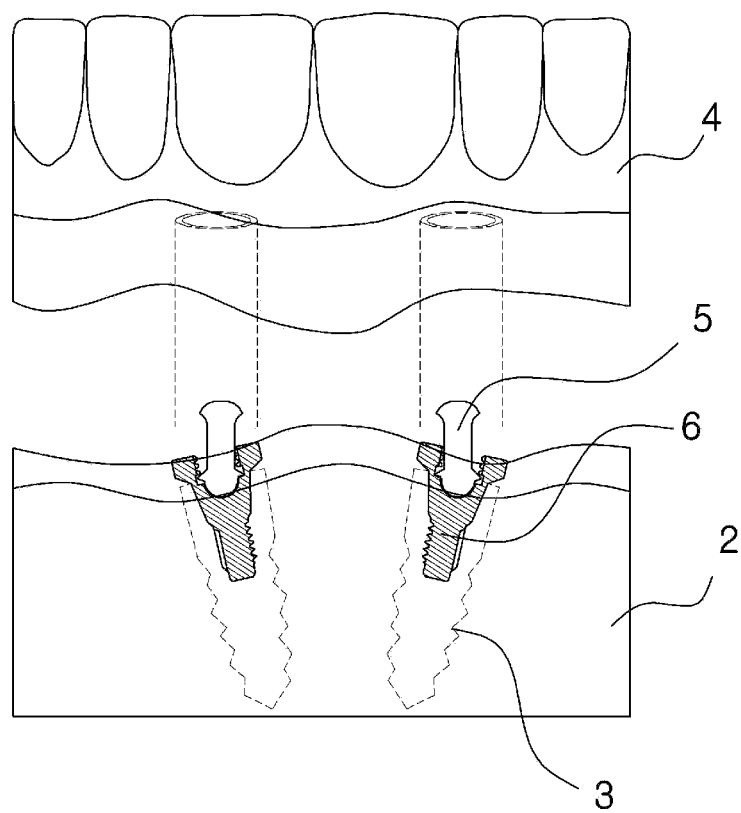
FIG. 4 is a schematic exemplary sectional view showing the in-use state of the denture-fixing attachment according to the embodiment.

FIGS. 2 to 4 are views showing a denture-fixing attachment according to one embodiment of the present invention. A denture-fixing attachment 1 according to the embodiment is configured to adjust the angle at which a denture 4 is fixed to a fixture 3 implanted into an alveolar bone 2, thereby freely connecting the denture 4 to the fixture 3 implanted in a slanted direction.

That is, an implant recess used to implant the fixture 3 is formed in the alveolar bone 2 using a tool such as, for example, a drill, the fixture 3 is implanted into the implant recess, and the attachment is fixed to the fixture 3 and serves as a connection component for connecting the denture 4 to the fixture 3.

The implant recess has female threads formed therein, and the fixture 3 has male threads formed in the outer peripheral surface thereof to mesh with the female threads, so that the fixture 3 is screwed to the implant recess.

The denture-fixing attachment 1 according to the embodiment includes a rod-shaped joint member 5, to an upper end of which the denture 4 is fixed, and an abutment 6 having a coupling portion formed in the outer surface of a lower portion thereof, which is coupled to a fixture recess formed in the fixture 3, and a receiving portion formed in an upper portion thereof, in which a lower portion of the joint member 5 is received.

That is, the denture-fixing attachment includes the abutment 6, which is coupled to the fixture 3, and the joint member 5, which is pivotably and rotatably jointed to the abutment 6 and is connected with the denture 4, so that the denture 3 is fixed to the alveolar bone 2.

Preferably, the aforementioned fixture recess is embodied as a spiral nut recess, and the coupling portion of the abutment 6 is embodied as male threads, which mesh with the fixture recess, so that the abutment 6 is screwed to the fixture 3.

In the above-described denture-fixing attachment 1 according to the embodiment, the receiving portion of the abutment 6 includes a receiving recess 7, into which the lower end 11 of the joint member 5 is inserted, and a stop protruding portion 10, which is provided in the receiving portion above the receiving recess 7 and has a guide groove 9, into which a locking protruding portion 8, protruding outward from the lower end 11 of the joint member 5, is fitted and which guides the coupling movement of the locking protruding portion 8.

That is, the locking protruding portion 8 of the joint member 5 is inserted into the guide groove 9 in the stop protruding portion 10 and is guided thereby, and the lower end 11 of the joint member 5 is received in the receiving recess 7, so that the lower end 11 of the joint member 5 freely pivots and rotates with respect to the inner peripheral surfaces of the receiving recess 7 and the stop protruding portion 10, thereby adjusting the angle formed by the upper end 12 of the joint member 5 and the abutment 6.

Therefore, even when the fixture 3 is implanted into the alveolar bone 2 in a slanted direction, the denture 4 is capable of being stably connected and fixed to the fixture 3.

In addition, the lower end 11 of the joint member 5 received in the receiving recess 7 is in contact with the stop protruding portion 10 provided above the receiving recess 7 so as to be prevented from being unexpectedly separated from the receiving recess 7, thereby enhancing stability without concern as to the release of the engagement of the denture 4 for a long time period.

That is, since the stop protruding portion 10, which functions to prevent the lower end 11 of the joint member 5 from being separated from the receiving recess 7, is integrally formed with the receiving recess 7, not only additional parts but also additional fastening elements are unnecessary, which enhances structural strength and enables stable long-term use.

In the above-described denture-fixing attachment 1 according to the embodiment, at least a predetermined portion of the guide groove 9 is preferably formed to extend in a horizontal direction in the inner peripheral surface of the stop protruding portion 10.

Accordingly, in the state in which the lower end 11 of the joint member 5 is guided along the inner peripheral surface of the stop protruding portion 10 and is received in the receiving recess 7, the locking protruding portion 8 is in contact with the horizontally extending portion of the guide groove 9 and is prevented from being separated from the receiving recess 7.

Figure 6:
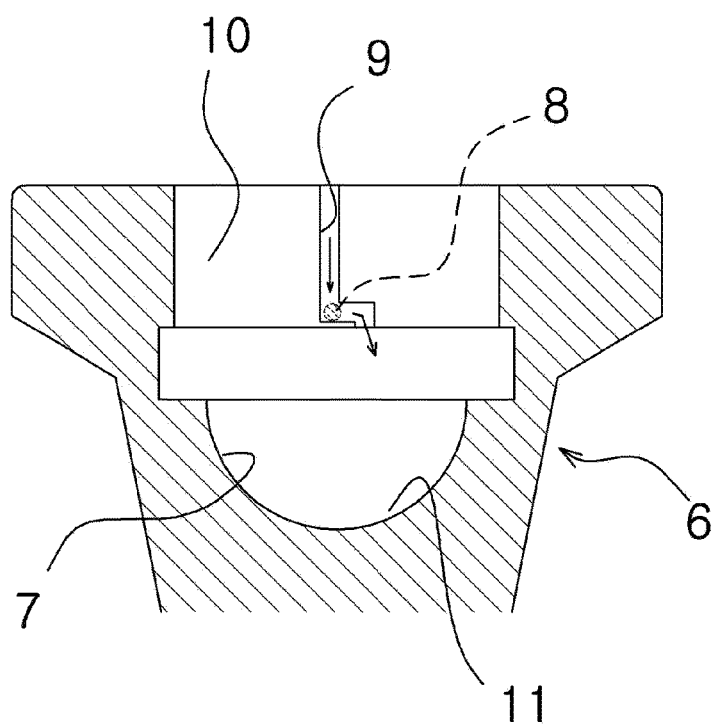
FIG. 6 is an exemplary partially enlarged sectional view showing an abutment applied to a denture-fixing attachment according to another embodiment of the present invention.

That is, the guide groove 9 may be formed to have an "L" shape or, as illustrated in FIG. 6, to have a "⌐" shape in the inner peripheral surface of the stop protruding portion 10, and in this case, the locking protruding portion 8 protrudes from the outer peripheral surface of the lower end of the joint member 5, and is fitted into the guide groove (for example, in a push-turn-push engagement manner).

Alternatively, the locking protruding portion 8 may be preferably formed to have an annular shape around the outer peripheral surface of the lower end of the joint member 5, so that the locking protruding portion 8 is screwed to the spiral guide groove 9.

Therefore, the annular-shaped locking protruding portion 8 provided at the lower end 11 of the joint member 5 is moved from the opening of the receiving portion to the receiving recess 7 through the screw-engagement with the spiral guide groove 9, and is prevented from being unexpectedly separated from the receiving recess 7.

Preferably, the bottom surface of the receiving recess 7 has a hemispherical shape, and the lower end 11 of the joint member 5 also has a hemispherical shape corresponding to the hemispherical-shaped receiving recess 7 so as to come into close contact with the bottom surface of the receiving recess 7, so that the lower end 11 of the joint member 5 easily pivots and rotates with respect to the bottom surface of the receiving recess 7.

More preferably, in the denture-fixing attachment 1 according to the embodiment constituted as above, both the upper end 12 and the lower end 11 of the joint member 5 have curved surfaces, more precisely hemispherical-shaped surfaces, and a connection portion 13 between the upper end 12 and the lower end 11 is formed to have a rod shape, which has a smaller diameter than the diameter of the upper end 12.

Accordingly, even when the upper end 12 of the joint member 5 is coupled to a portion of the denture 4 at a certain inclination angle, the maximum possible area for close contact between the upper end 12 of the joint member 5 and the denture 4 can be secured.

Further, since the angle at which the joint member 5 can pivot with respect to the receiving portion is decided depending on the diameter of the connection portion 13, a user may select a connection portion having a suitable shape, and may use the same.

Figure 5:
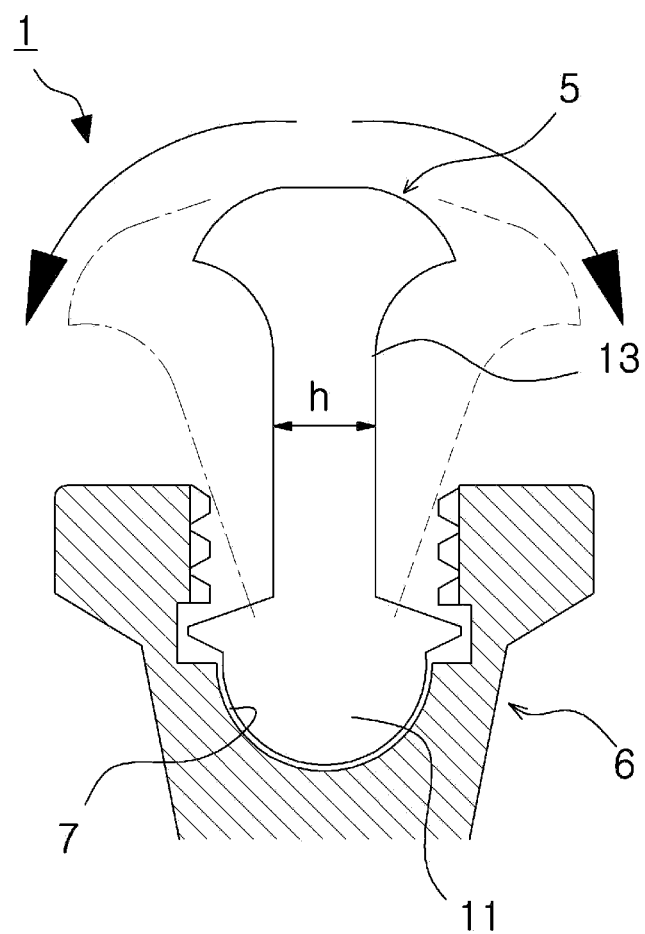
FIG. 5 is an exemplary partially enlarged sectional view showing the denture-fixing attachment according to one embodiment of the present invention.

That is, as illustrated in FIGS. 3 and 5, the smaller the diameter H or h of the connection portion 13, the larger the pivot range, and accordingly a user may simply select a joint member having a suitable shape for the dental treatment, and assemble and use the same.

The operational effects of the denture-fixing attachment according to the embodiment constituted as above will now be explained in detail.

When a dental treatment of fixing the denture 4 is performed using the denture-fixing attachment 1 according to the embodiment, as illustrated in FIG. 4, the fixture 3 is first implanted into the alveolar bone 2 as described above.

Subsequently, the joint member 5 is fastened to the receiving portion of the abutment 6 in a screw-engagement manner so that the lower end 11 of the joint member 5 is inserted and received in the receiving recess 7, and the attachment 1, formed through the assembly of the abutment 6 and the joint member 5, is fastened to the fixture recess of the fixture 3.

As such, when the attachment 1 is coupled to the fixture 3, a fixing portion of the denture 4 is fixedly coupled to the upper end 12 of the joint member 5, thereby completing the denture-fixing treatment.

Depending on the treatment conditions, for example, in the case in which the denture 4 is connected to the fixture 3 implanted into the alveolar bone 2 in a slanted direction, the treatment can be carried out after the angle of the joint member 5 with respect to the receiving recess 7 is adjusted by pivoting the joint member 5.

As described above, the denture-fixing attachment according to the embodiment has an economic effect due to the simple structure of the abutment to which the joint member is pivotably coupled, highly efficient workability due to a simplified assembly process, and increased stability in long-term use due to structural stability in that the receiving recess and the stop protruding portion, which constitute the receiving portion, are integrally formed.

The embodiment of the present invention as described above is only illustrative, and it will be understood by those skilled in the art that various modifications and other equivalent exemplary embodiments may be made. Therefore, it will be understood that the present invention is not limited only to the forms mentioned in the detailed description. Accordingly, the true technical scope of the present invention should be defined by the technical spirit of the appended claims. In addition, it is to be understood that the present invention includes all modifications, equivalents, and substitutions which fall within the spirit and scope of the present invention as defined by the appended claims.

The present invention relates to a denture-fixing attachment used to fix a denture after a dental implant treatment and, more particularly, to a denture-fixing attachment, which has an economic effect due to a simple structure and consequent improvement of productivity, highly efficient workability due to a simplified assembly process, and increased stability in use due to the secure maintenance of engagement force for a long time period and the consequent prevention of unexpected release of engagement, and therefore, the present invention has industrial applicability.

The invention claimed is:

1. A denture-fixing attachment for freely connecting a denture to a fixture implanted into an alveolar bone in a slanted direction by adjusting a denture angle of the denture with respect to the fixture, the denture-fixing attachment comprising:

a rod-shaped joint member having an upper end for supporting the denture fixed thereto and a locking protruding portion protruding laterally from a lower portion of the joint member; and an abutment having a coupling portion formed in an outer surface of a lower portion thereof so as to be coupled to a fixture recess formed in the fixture, and a receiving portion formed in an upper portion thereof so as to receive the lower portion of the joint member therein, wherein the receiving portion of the abutment includes a receiving recess for receiving the lower portion of the joint member inserted thereinto, and a stop protruding portion provided in the receiving portion above the receiving recess and having a guide groove disposed adjacent to the stop protruding portion for guiding coupling movement of the locking protruding portion fitted thereinto, wherein the guide groove includes a first guide groove part formed in a vertical direction, a second guide groove part formed at an end of the first guide groove part in a horizontal direction, and a third guide groove part formed at an end of the second guide groove part in the vertical direction, and wherein a bottom end of the vertical third guide groove part is open downward along the vertical direction at a distal end thereof, such that the locking protruding portion moves through and out of the guide groove and into the receiving recess as the joint member is inserted thereinto.

* * * * *